(12) United States Patent
Kim et al.

(10) Patent No.: US 12,029,730 B2
(45) Date of Patent: Jul. 9, 2024

(54) PHARMACEUTICAL COMPOSITION FOR PREVENTING OR TREATING CANCER, CONTAINING N-1H-BENZIMIDAZOL-2-YL-3-(1H-PYRROLE-1-YL)BENZAMIDE AS ACTIVE INGREDIENT

(71) Applicant: KOREA INSTITUTE OF RADIOLOGICAL & MEDICAL SCIENCES, Seoul (KR)

(72) Inventors: Jae Sung Kim, Namyangju-si (KR); Ah Young Kim, Seoul (KR); Sang Gu Hwang, Seoul (KR); Jie Young Song, Seoul (KR); Yi Na Yoon, Incheon (KR)

(73) Assignee: KOREA INSTITUTE OF RADIOLOGICAL & MEDICAL SCIENCES, Seoul (KR)

( * ) Notice: Subject to any disclaimer, the term of this patent is extended or adjusted under 35 U.S.C. 154(b) by 597 days.

(21) Appl. No.: 17/285,464

(22) PCT Filed: Sep. 3, 2019

(86) PCT No.: PCT/KR2019/011332
§ 371 (c)(1),
(2) Date: Apr. 14, 2021

(87) PCT Pub. No.: WO2020/085642
PCT Pub. Date: Apr. 30, 2020

(65) Prior Publication Data
US 2021/0379022 A1    Dec. 9, 2021

(30) Foreign Application Priority Data
Oct. 23, 2018  (KR) .................. 10-2018-0126869

(51) Int. Cl.
*A61K 31/4184* (2006.01)
*A23L 33/10* (2016.01)
*A61P 35/00* (2006.01)

(52) U.S. Cl.
CPC .......... *A61K 31/4184* (2013.01); *A23L 33/10* (2016.08); *A61P 35/00* (2018.01); *A23V 2002/00* (2013.01)

(58) Field of Classification Search
CPC .................................................. A61K 31/4184
See application file for complete search history.

(56) References Cited

U.S. PATENT DOCUMENTS

| | | | |
|---|---|---|---|
| 2008/0021027 A1 | 1/2008 | Benson et al. | |
| 2013/0225810 A1 | 8/2013 | Bai et al. | |
| 2014/0343086 A1 | 11/2014 | Dodd et al. | |
| 2015/0158878 A1 | 6/2015 | Leban et al. | |

FOREIGN PATENT DOCUMENTS

| | | |
|---|---|---|
| KR | 10-2009-0016605 A | 2/2009 |
| KR | 10-2011-0076190 A | 7/2011 |
| KR | 10-2013-0083921 A | 7/2013 |
| KR | 10-2015-0020170 A | 2/2015 |
| KR | 10-1700599 B1 | 1/2017 |

OTHER PUBLICATIONS

International Search Report for PCT/KR2019/011332 mailed Dec. 6, 2019 from Korean Intellectual Property Office.

*Primary Examiner* — Golam M Shameem
(74) *Attorney, Agent, or Firm* — Revolution IP, PLLC (57) ABSTRACT

The present invention relates to a pharmaceutical composition for preventing or treating cancer, a radiosensitizer composition for treating cancer, and a health functional food for preventing or improving cancer, which comprise N-1H-benzimidazol-2-yl-3-(1H-pyrrol-1-yl) benzamide, a derivative thereof, or a pharmaceutically acceptable salt thereof as an active ingredient. The pharmaceutical composition comprising N-1H-benzimidazol-2-yl-3-(1H-pyrrol-1-yl) benzamide or a derivative thereof as an active ingredient according to the present invention arrests the mitosis of cancer cells to prevent proliferation and at the same time, to exhibit low toxicity in normal cell lines and induce apoptosis only in cancer cell lines, so it can be used as an effective anticancer agent. In addition, the N-1H-benzimidazol-2-yl-3-(1H-pyrrol-1-yl) benzamide of the present invention can increase the sensitivity of the treated cancer cells to radiation, so it can be used as a radiosensitizer composition for cancer treatment.

7 Claims, 9 Drawing Sheets

PHARMACEUTICAL COMPOSITION FOR PREVENTING OR TREATING CANCER, CONTAINING N-1H-BENZIMIDAZOL-2-YL-3-(1H-PYRROLE-1-YL)BENZAMIDE AS ACTIVE INGREDIENT

CROSS REFERENCE TO PRIOR APPLICATIONS

This application is a National Stage Application of PCT International Patent Application No. PCT/KR2019/011332 filed on Sep. 3, 2019, under 35 U.S.C. § 371, which claims priority to Korean Patent Application No. 10-2018-0126869 filed on Oct. 23, 2018, respectively, which are all hereby incorporated by reference in their entirety.

TECHNICAL FIELD

The present invention relates to a pharmaceutical composition for preventing or treating cancer, a radiosensitizer composition for treating cancer, and a health functional food for preventing or improving cancer, which comprise N-1H-benzimidazol-2-yl-3-(1H-pyrrol-1-yl) benzamide, a derivative thereof, or a pharmaceutically acceptable salt thereof as an active ingredient.

BACKGROUND ART

In an effective and traditional treatment method for diseases caused by the failure of normal gene control, typically referred to as cancer, the tumor is surgically excised and removed, but when the primary cancer is metastasized to other organs, surgical operation is not possible, so anticancer drug therapy is widely used. Anticancer agents used in the drug treatment are mainly used by synthesizing monomolecular substances by organic or inorganic methods. Traditional drug therapy in this manner involves many side effects, one of which is that the substance used as a drug is an artificially synthesized substance derived from external bodies and that the site of action of anticancer substance targets a protein that has already overexpressed.

'Cancer' refers to a group of diseases characterized by excessive cell proliferation and invasion into surrounding tissues when the normal apoptosis balance is broken. Among them, breast cancer, in particular, is a cancer with an incidence of 25.2% among female cancers worldwide, and between 2008 and 2012, the incidence of breast cancer continued to rise, increasing by about 20%. Korea has an incidence rate of 52.1%, which is one of the countries with a high incidence of breast cancer among OECD countries, and it is widely known that breast cancer treatment methods differ depending on the presence or absence of hormone-responsive receptors. In order to treat such breast cancer, surgery, chemotherapy, radiation therapy, and hormone therapy are combined depending on the progression.

Until now, many natural products, protein or peptide anticancer drugs, and chemo-synthetic anticancer drugs have been developed and used, but most of them show serious side effects that affect normal cells in vivo, and generally do not show the same therapeutic effect depending on the carcinoma or depending on the patient even the same carcinoma.

In particular, radiation therapy is an essential treatment method for various cancers as a method for treating cancer, but acquisition of radioresistance of cancer cells and damage to normal tissues during high-dose radiation treatment are constantly being pointed out as problems that reduce the efficiency of radiation treatment. Accordingly, there is a growing need for a substance capable of increasing the effect of radiation therapy in a method for treating cancer cells.

Therefore, there is a need for a lot of research to develop a new concept anticancer agent that solves the above problems worldwide which can selectively remove only cancer cells without affecting normal cells in vivo, and can further increase the sensitivity of cancer cells to radiation.

DISCLOSURE

Technical Problem

Accordingly, the present inventors were studying a substance having anticancer activity and radiation sensitivity and confirmed that the treatment with N-1H-benzimidazol-2-yl-3-(1H-pyrrole-1-yl) benzamide, among substances that inhibit the activity of MASTL kinase in the breast cancer cell line MCF7, suppressed the proliferation of the cancer cell line and increased the radiation treatment effect, and completed the present invention.

Therefore, an object of the present invention is to provide a pharmaceutical composition for preventing or treating cancer, a radiosensitizer composition for treating cancer, and a health functional food for preventing or improving cancer, which comprise N-1H-benzimidazol-2-yl-3-(1H-pyrrol-1-yl) benzamide, a derivative thereof, or a pharmaceutically acceptable salt thereof as an active ingredient:

Technical Solution

In order to achieve the above object, the present invention provides a pharmaceutical composition for preventing or treating cancer comprising N-1H-benzimidazol-2-yl-3-(1H-pyrrol-1-yl) benzamide, a derivative thereof, or a pharmaceutically acceptable salt thereof as an active ingredient.

Also, the present invention provides a radiosensitizer composition for treating cancer comprising N-1H-benzimidazol-2-yl-3-(1H-pyrrol-1-yl) benzamide or a derivative thereof as an active ingredient.

In addition, the present invention provides a health functional food for preventing or improving cancer comprising N-1H-benzimidazol-2-yl-3-(1H-pyrrol-1-yl) benzamide or a derivative thereof, as an active ingredient.

Advantageous Effects

The pharmaceutical composition comprising N-1H-benzimidazol-2-yl-3-(1H-pyrrol-1-yl) benzamide or a derivative thereof as an active ingredient according to the present invention inhibits mitosis of cancer cells to prevent proliferation and at the same time, to exhibit low toxicity in normal cell lines and induce apoptosis only in cancer cell lines, so it can be used as an effective anticancer agent. In addition, the N-1H-benzimidazol-2-yl-3-(1H-pyrrol-1-yl) benzamide of the present invention can increase the sensitivity of the treated cancer cells to radiation, so it can be used as a radiosensitizer for cancer treatment.

BEST MODE

The present invention provides a pharmaceutical composition for preventing or treating cancer comprising N-1H-benzimidazol-2-yl-3-(1H-pyrrol-1-yl) benzamide, a derivative thereof, or a pharmaceutically acceptable salt thereof as an active ingredient.

Hereinafter, the present invention will be described in more detail.

N-1H-benzimidazol-2-yl-3-(1H-pyrrol-1-yl) benzamide (MKI-1) contained as an active ingredient of the present invention inhibits the activity of MASTL kinase and arrests the mitosis of cancer cells thereby inhibiting the proliferation of cancer cells. In addition, since it exhibits low toxicity in normal cell lines and can induce apoptosis only in cancer cell lines, it can be easily used as an anticancer agent and the chemical formula thereof is as follows.

[Chemical Formula]

The MASTL (microtubule-associated serine/threonine kinase-like) kinase, of which the activity the pharmaceutical composition of the present invention inhibits, is an enzyme that plays an important role in cell division and it is widely known to phosphorylate ENSA (α-endosulfine) and ARPP19 (cAMP-regulated phosphoprotein 19) proteins. In addition, it is known that when MASTL is highly expressed in prostate cancer, lung cancer and gastric cancer including breast cancer, the prognosis is poor. Accordingly, the inventors of the present invention confirmed that when cancer cells are treated with N-1H-benzimidazol-2-yl-3-(1H-pyrrol-1-yl) benzamide (MKI-1), which effectively inhibits the MASTL kinase, only the cancer cells can be effectively killed, and completed the present invention.

In addition, the pharmaceutical composition of the present invention can inhibit the expression level of phosphorylated endosulfine alpha, arrest the mitosis of cancer cells, or induce the apoptosis of cancer cells, thereby effectively inhibiting the proliferation of cancer cells.

Furthermore, the pharmaceutical composition according to the present invention may include 5 to 150 μM of N-1H-benzimidazol-2-yl-3-(1H-pyrrol-1-yl) benzamide (MKI-1), preferably 10 to 120 μM, and more preferably 30 to 100 μM of effective concentration, as an active ingredient.

The pharmaceutical composition of the present invention may include at least one of pharmaceutically acceptable carriers such as saline, sterile water, Ringer's solution, buffered saline, cyclodextrin, dextrose solution, maltodextrin solution, glycerol, ethanol, liposomes, and if necessary, may further include other conventional additives such as antioxidants and buffers, in addition to N-1H-benzimidazol-2-yl-3-(1H-pyrrol-1-yl) benzamide (MKI-1), a derivative thereof, or a pharmaceutically acceptable salt thereof. In addition, it may additionally include diluents, dispersants, surfactants, binders, and/or lubricants to prepare injectable formulations such as aqueous solutions, suspensions, emulsions, etc., pills, capsules, granules, or tablets. Furthermore, it may be preferably formulated according to each component by an appropriate method in the art or by using a method disclosed in Remington's Pharmaceutical Science, Mack Publishing Company, Easton PA The pharmaceutical composition of the present invention is not particularly limited in its formulation, but is preferably formulated as an injection or inhalant.

The method of administering the pharmaceutical composition of the present invention is not particularly limited, but may be administered parenterally, e.g., intravenously, subcutaneously, intraperitoneally, by inhalation or topically, or orally depending on the intended method. The dosage range varies depending on the patient's weight, age, sex, health condition, diet, administration time, administration method, excretion rate, and severity of disease. The daily dosage refers to an amount of a therapeutic substance of the present invention sufficient to treat a disease state alleviated by being administered to an individual in need of treatment. The effective amount of a therapeutic substance depends on the particular compound, the disease state and its severity, the individual in need of treatment, which can be determined routinely by a person skilled in the art. As a non-limiting example, the dosage of the composition according to the present invention to the human body may vary depending on the patient's age, weight, sex, dosage form, health condition, and degree of disease, and it is generally 0.0001 to 1000 mg/day, preferably 1 to 500 mg/day, based on an adult patient weighing 70 kg and may be administered in divided doses from once a day to several times a day at regular time intervals.

As used herein, the term 'individual' means a subject in need of the treatment for cancer, and more specifically, human or non-human primates, mammals such as mice, rats, dogs, cats, horses and cattle.

As used herein, the term 'cancer' refers to a group of diseases having characteristics that cells overproliferate and infiltrate into surrounding tissues when the normal apoptosis balance is broken. Cancer of the present invention may be at least one selected from the group consisting of brain tumor, benign astrocytoma, malignant astrocytoma, pituitary adenoma, meningioma, cerebral lymphoma, oligodendroglioma, intracranial tumor, ependymoma, brain stem tumor, head and neck tumor, laryngeal cancer, oropharyngeal cancer, nasal and paranasal cavity cancer, nasopharyngeal cancer, salivary gland cancer, hypopharyngeal cancer, thyroid cancer, thoracic tumor, small cell lung cancer, non-small cell lung cancer, thymus cancer, mediastinal tumor, esophageal cancer, breast cancer, male breast cancer, abdominal tumor, gastric cancer, liver cancer, gallbladder cancer, biliary tract cancer, pancreatic cancer, small intestine cancer, colon cancer, anal cancer, bladder cancer, kidney cancer, male genital tumor, penile cancer, urethral cancer, prostate cancer, female genital tumor, cervical cancer, endometrial cancer, ovarian cancer, uterine sarcoma, vaginal cancer, vulva cancer, female urethral cancer, skin cancer, myeloma, leukemia and malignant lymphoma, preferably prostate cancer, lung cancer and stomach cancer including breast cancer, and most preferably breast cancer, but it is not limited thereto. The present invention can be applied to all types of cancer species that may exhibit anticancer effects due to inhibition of MASTL kinase activity.

The pharmaceutical composition of the present invention can be used in combination with radiation therapy, and in particular, the pharmaceutical composition of the present invention can increase the sensitivity to radiation even with respect to cancer cells or cancer cells having radioresistance and thus when treating cancer cells in combination with radiation therapy, there is a characteristic that can increase the effect of radiation therapy.

In addition, the present invention provides a radiosensitizer composition for treating cancer comprising N-1H-benzimidazol-2-yl-3-(1H-pyrrol-1-yl) benzamide or a derivative thereof, as an active ingredient:

The treatment of cancer cells with N-1H-benzimidazol-2-yl-3-(1H-pyrrol-1-yl) benzamide or a derivative thereof of the present invention increases the sensitivity of cancer cells to radiation, thereby promoting the death of cancer cells.

The criterion of radiation sensitivity or radioresistance can be classified by the slope value of a linear model created using the cell survival rate when irradiated with 0 to 2.5 Gy of gamma radiation. This classification method has been reported by Jerry R. Williams et al. in his paper (Acta Oncologica, 46, 628-638, 2007). As used herein, the term "radiation sensitivity" refers to a cell having the range of 0.00 to 0.30 of the slope values, and "radioresistance" refers to a cell having the range of 0.31 to 1.00 of the slope values.

SW1222, HCT116, LoVo, CBS, LS174T, 379.2, 80S4 and N6CH3 are known as radiation-sensitive cells, and DLD-1, HT29, WiDR, SW480, SW116, 19S186, Caco2, Caco2-neoras, U251, U87 and T98G are known as the radiation resistant cells, and as a specific example of the present invention, $CD44^{high}/CD24^{low}$ MCF7 cells were used as radiation-resistant cells.

In the present invention, the cancer may be at least one selected from the group consisting of brain tumor, benign astrocytoma, malignant astrocytoma, pituitary adenoma, meningioma, cerebral lymphoma, oligodendroglioma, intracranial tumor, ependymoma, brain stem tumor, head and neck tumor, laryngeal cancer, oropharyngeal cancer, nasal and paranasal cavity cancer, nasopharyngeal cancer, salivary gland cancer, hypopharyngeal cancer, thyroid cancer, thoracic tumor, small cell lung cancer, non-small cell lung cancer, thymus cancer, mediastinal tumor, esophageal cancer, breast cancer, male breast cancer, abdominal tumor, gastric cancer, liver cancer, gallbladder cancer, biliary tract cancer, pancreatic cancer, small intestine cancer, colon cancer, anal cancer, bladder cancer, kidney cancer, male genital tumor, penile cancer, urethral cancer, prostate cancer, female genital tumor, cervical cancer, endometrial cancer, ovarian cancer, uterine sarcoma, vaginal cancer, vulva cancer, female urethral cancer, skin cancer, myeloma, leukemia and malignant lymphoma, preferably prostate cancer, lung cancer and stomach cancer including breast cancer, and most preferably breast cancer, but it is not limited thereto.

The radiosensitizer composition for radiation therapy of cancer cells according to the present invention may be used in combination with radiation therapy.

The radiation therapy used in the present invention is a local treatment method for damaging the DNA of malignant cells. Normal cells have a greater ability to repair this damage than tumor cells, and the radiotherapy is known to take advantage of this difference.

The radiation therapy may include external beam radiation (x-rays, γ-rays, protons and neutrons), brachytherapy and radioactive material implantation, and may be administered by 2-D, 3-D, confocal, intensity-modulated radiation therapy (IMRT) and image-guided radiation therapy (IGRT) approaches. Standard radiation therapy that can be used in cancer treatment of the present invention may be a method of providing a total dose of about 60 Gys (50 to 70 Gys) at 2.5 Gy/day. However, one of ordinary skill in the art can select the desired radiation dose based on the particular subject, device and tumor type.

The radiosensitizer composition according to the present invention improves the existing radiation therapy by increasing the sensitivity of cancer cells to radiation. For example, the use of the radiosensitizer composition of the present invention makes cancer cells at least 30%, 40%, 50%, 60%, 70%, 80%, 90%, 100% or more sensitive to radiation. As used herein, the terms "sensitivity" and "radiation sensitivity" refer to the number of surviving cells based on radiation dose. Therefore, an increase in radiation sensitivity may mean a decrease in the number of cells surviving at a certain radiation dose, a decrease in radiation dose required for a lethal dose, or a combination thereof.

Since the radiosensitizer of the present invention can increase sensitivity not only in radiation therapy of cancer cells, but also in chemotherapy, the use of the radiosensitizer of the present invention as a sensitizer to increase sensitivity in chemotherapy may also fall within the scope of the present invention.

In addition, the present invention provides a health functional food for preventing or improving cancer comprising N-1H-benzimidazol-2-yl-3-(1H-pyrrol-1-yl) benzamide or a derivative thereof as an active ingredient.

In the present invention, the term "health functional food" refers to a food manufactured and processed by extracting, concentrating, refining, mixing specific ingredients as raw materials or specific ingredients in food raw materials for the purpose of health care, and it refers to foods designed and processed to sufficiently exert biological control functions such as biological and defense, biological rhythm control, disease prevention and recovery, etc. by the above ingredients, and thus it can perform functions related to disease prevention or health recovery.

When N-1H-benzimidazol-2-yl-3-(1H-pyrrol-1-yl) benzamide or a derivative thereof according to the present invention is used as a health functional food, it can be added as it is or together with other food or food ingredient, which can be appropriately used by selecting as required.

In addition, there is no particular limitation on the kind of health functional food in which the N-1H-benzimidazol-2-yl-3-(1H-pyrrol-1-yl) benzamide or a derivative thereof according to the present invention can be used. For example, there are ramen, other noodles, beverages, tea, drinks, alcoholic beverages, various soups, meats, sausages, bread, chocolate, candy, confectionery, pizza, gum, dairy products including ice cream, or vitamin complexes and the like. In addition, the health functional food according to the present invention may include suitable auxiliary ingredients and known additives which can be usually added to the health functional food according to the choice of a skilled person in addition to N-1H-benzimidazol-2-yl-3-(1H-pyrrol-1-yl) benzamide.

Hereinafter, the present invention will be described in more detail through examples. These examples are only intended to illustrate the present invention in more detail, and it will be apparent to those skilled in the art that the scope of the present invention is not limited by these examples according to the gist of the present invention. The examples of the present invention are provided to more completely explain the present invention to those of ordinary skill in the art.

EXAMPLE

Example 1. Preparation of a Single Compound for Selection of MASTL Kinase Inhibitors and Cell Lines Used and Methods of Culturing the Same In silico-based single compounds of 40 for screening MASTL kinase inhibitors were purchased from Cambridge Corporation, the pan-AGC kinase inhibitor AT13148 was purchased from Selleck Chemicals, and the MASTL kinase inhibitor GKI-1 was purchased from Korea Research Institute of Chemical Technology.

In addition, the cell line in this experiment was distributed from ATCC (American Type Culture Collection; Manassas, VA). Human-derived tumor cell lines, breast cancer cell lines MCF7 and T47D was cultured in DMEM medium containing 10% fetal bovine serum (FBS; HyClone, South Logan, UT) and 1% penicillin/streptomycin (Corning, NY, USA) at 37° C. and 5% $CO_2$, and the BT549 breast cancer cell line was cultured in RPMI 1640 (Welgene, Daegu, Korea) as a medium used under the same conditions. Human-derived normal cell line MCF10A was cultured in DMEM/F12 (Invitrogen) medium containing 5% horse serum (Invitrogen), 1% penicillin/streptomycin, 20 ng/ml EGF (Peprotech, London, UK), 0.5 mg/ml hydrocortisone (Sigma-Aldrich, MO, USA), 100 ng/ml cholera toxin (Cholera Toxin, Sigma-Aldrich) and 10 μg Insulin (Sigma-Aldrich) at 37° C. and 5% $CO_2$.

In addition, a surface marker of $CD44^{high}/CD24^{low}$ MCF7 cell line having radioresistance was identified by using FACS Aria II (BD Biosciences, CA, USA), and was isolated from the MCF7 cell line, and whether the isolated cell line had a radioresistant phenotype was selected by judging whether the cell line formed colonies or spheres after exposure to radiation.

Thereafter, the cell line and compound prepared through the method of Example 1 were used in the following examples.

Example 2. Selection of MASTL (Microtubule-Associated Serine/Threonine Kinase-Like) Kinase Inhibitors MASTL kinase is an M-phase entry regulator of mitosis that has the activity of inducing the inactivation of PP2A by inhibiting ARPP19 and ENSA phosphorylation. Cancer cells are immortalized cells that are constantly dividing out of the normal cell cycle, but cancer cells that proliferate without limitation can be killed by using an inhibitor that inhibits MASTL kinase acting as the M-phase regulator as described above. An experiment was performed to find an inhibitor that can effectively inhibit the activity of MASTL.

First, among the libraries of 500 compounds capable of inhibiting MASTL kinase, the candidates of 40 compounds that effectively inhibit the activity were selected. Thereafter, in order to find a substance that specifically exhibits apoptosis effect only on cancer cells among the 40 candidate substances and does not exhibit toxicity in normal cells, WST-8 analysis (Cyto X™ cell viability assay kit, LPS solution, Daejeon, Korea) was performed according to the manufacturer's protocol. Briefly, MCF7 and MCF10A cells were seeded into 96-well plates, incubated for 24 hours, and then was treated with 42 inhibitor candidates. Among the compounds, the multi-AGC kinase inhibitor AT13148 was used as a positive control. Thereafter, the absorbance was measured at 450 nm using a Versamax microplate reader (Molecular Devices, CA, USA), and the results of the experiment were shown in FIG. 1A.

In addition, an immunoblotting experiment was performed to confirm whether the candidate substances effectively inhibit MASTL activity. The MASTL kinase analysis in vitro was performed by reacting recombinant GST-tagged-MASTL (Thermo Fisher Scientific, Waltham, MA, USA) and his-tagged-ENSA (Sino Biological Inc., Beijing, China) proteins or immunoprecipitated proteins derived from MCF7 cells with the MASTL antibody (AP7147d; Abgent, CA, USA) in a kinase buffer consisting of 100 mM Tris-HCl (pH 7.5), 30 mM $MgCl_2$, 2 mM DTT, 1 mM EDTA and 10 μM ultrapure ATP. The reaction proceeded, and then stopped by treating with SDS-loading buffer. In this experiment, the multi-AGC kinase inhibitor AT13148 was used as a positive control. The reaction was analyzed by performing immunoblotting for phosphorylated ENSA, and the results of the analysis were shown in FIG. 1B, and the results of the experiments confirming the cell survival and the kinase inhibitor activity were shown in FIG. 1C.

Figure 1A:
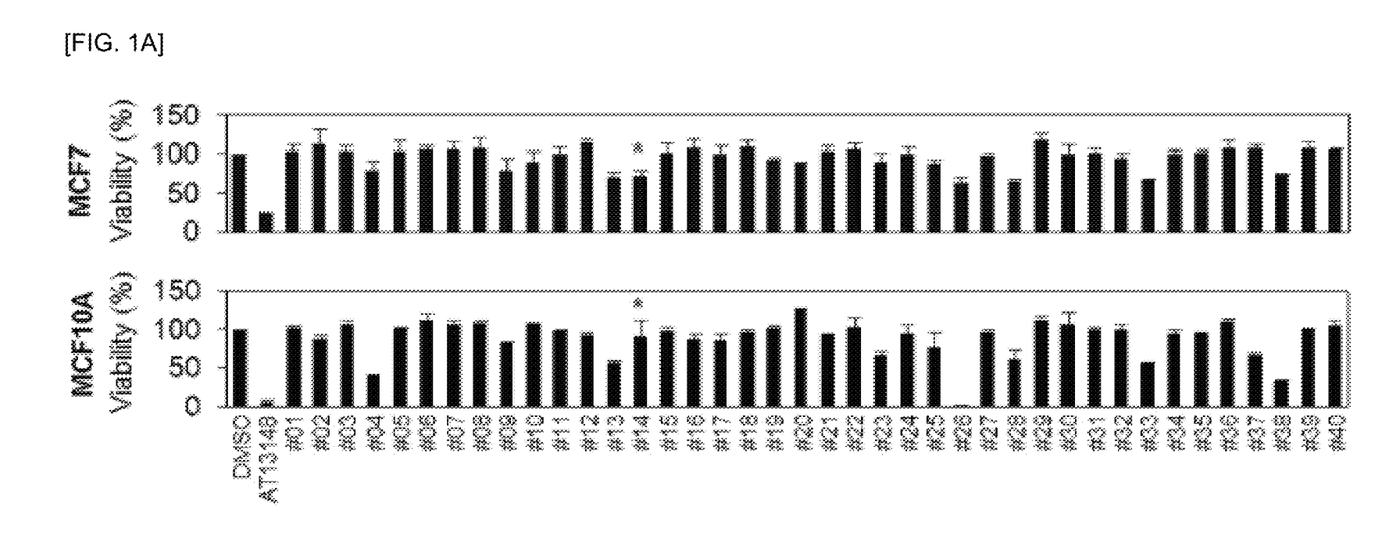
FIG. 1A shows the cell viability when a breast cancer cell line (MCF7) and a normal cell line (MCF10A) were treated with 42 single compounds.

As shown in FIG. 1A, it was confirmed that when #14 and #38 among about 40 candidate compounds were treated, the growth of the treated cancer cell line (MCF7) was significantly inhibited, thereby inhibiting the proliferation of cancer cells to exhibit the anticancer effect. It was possible to confirm that the anticancer effect appeared. It was confirmed that when the normal cell line (MCF10A) was treated with

38, the cell viability was significantly lowered to 50% and less, on the other hand, when the cell line was treated with #14, another candidate material, the cell viability was maintained as high as that of the control group DMSO.

Figure 1B:
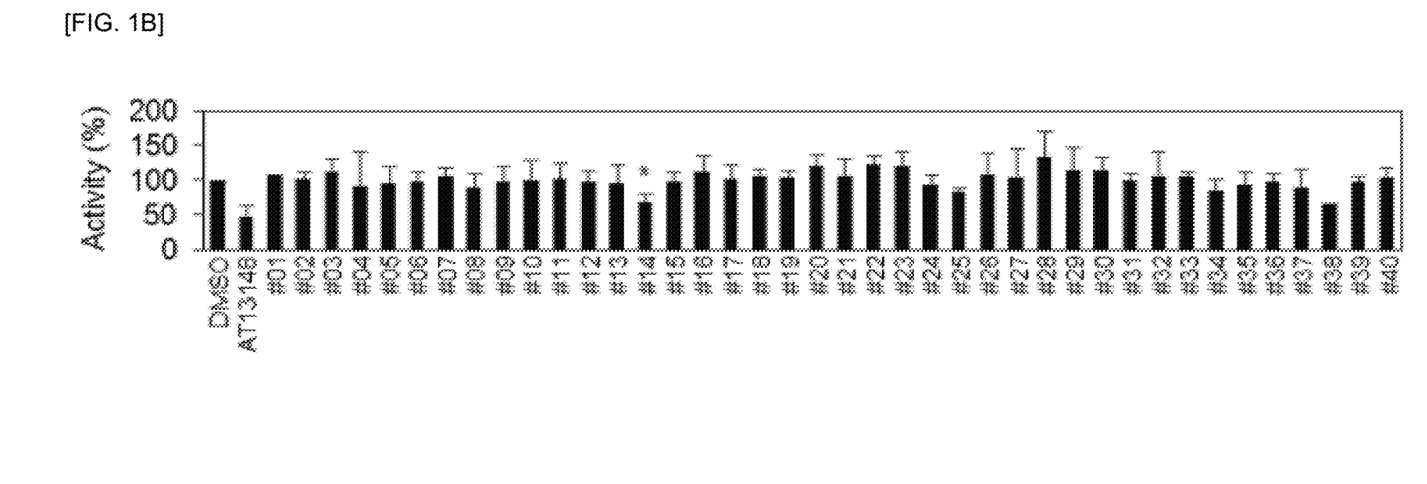
FIG. 1B shows the degree of inhibition of MASTL kinase activity after treatment of 42 single compounds.

In addition, as confirmed in FIG. 1B, when cancer cells were treated with #14 and #38 of the 42 candidate substances, the MASTL kinase activity was reduced to 50% or less, similar to kinase inhibitory effect of the positive control AT13148.

Figure 1C:
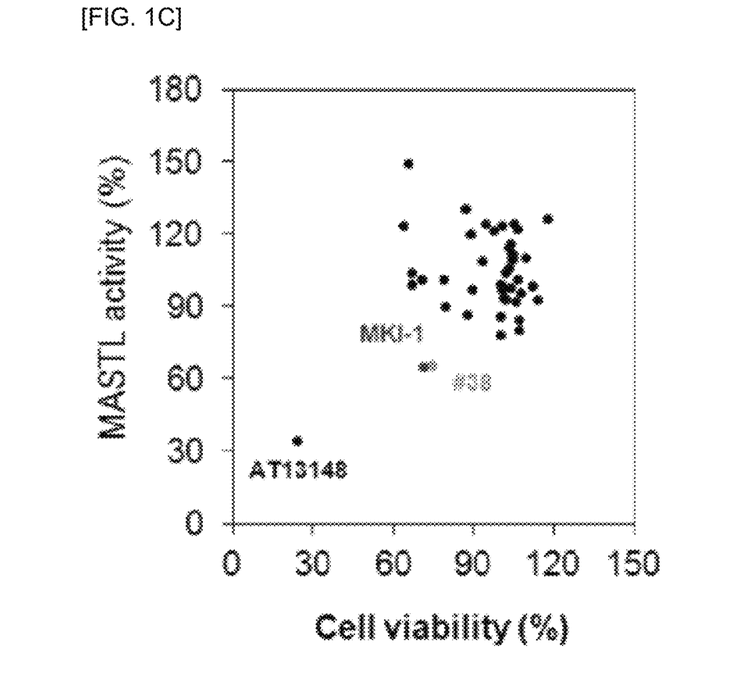
FIG. 1C shows the result of integrating the degree of inhibition of MASTL kinase activity and the cell viability after treatment of 42 single compounds in one figure.

Overall, candidate that does not show toxicity in normal cells, but exhibits a specific killing effect in cancer cells, and especially can inhibit MASTL kinase activity the most was confirmed in FIG. 1C to identify candidate #14, that is, N-1H-benzimidazol-2-yl-3-(1H-pyrrol-1-yl) benzamide. In particular, it was confirmed that N-1H-benzimidazol-2-yl-3-(1H-pyrrol-1-yl) benzamide has the potential to be used as an anticancer agent, considering that in order to be used as an anticancer agent, it is necessary to minimize side effects to act specifically only on cancer cells without affecting normal cells.

Example 3. Confirmation of MASTL Kinase Inhibitory Activity of N-1H-benzimidazol-2-yl-3-(1H-pyrrol-1-yl) benzamide Selected In Vitro An experiment of ADP-Glo™ luminescence-kinase analysis was performed to confirm that the selected N-1H-benzimidazol-2-yl-3-(1H-pyrrol-1-yl) benzamide (MKI-1) can effectively inhibit MASTL in vitro.

A protein kinase analysis was performed using the ADP-Glo™ kinase assay kit according to the standard protocol provided by Promega. The ADP-Glo™ luminescence-kinase assay was measured by converting ADP produced by Promega's MASTL kinase into a luminescent signal, and the decrease in the luminescent signal means a decrease in ADP production, which suggests that the activity of MASTL kinase was effectively inhibited. A solution of a serial 2-fold dilution of the MASTL kinase inhibitor (GKI-1, MKI-1 or AT13148) was prepared and MASTL kinase 25n, ENSA 250 ng and 10 μM ATP was mixed in a kinase reaction buffer consisting of 100 mM Tris-HCl (pH 7.5), 30 mM $MgCl_2$, 2 mM DTT, 1 mM EDTA and 10 μM ultra-pure ATP (Promega). Thereafter, the mixture was reacted at 30° C. for 30 minutes in an E-tube, and a kinase detection reagent was added thereto, followed by reacting for 30 minutes to detect the converted ATP. Then, the reacted product was transferred to a 384-well white plate, and fluorescence was read using a SpectraMax i3x Multi-Mode Microplate Reader (Molecular Devices), and GKI-1, N-(4-chlorophenyl)-3-(1H-pyrazol-4-yl)aniline and AT13148 were used as positive controls. The effect of inhibiting kinase activity of GKI-1 and MKI-1 and its $IC_{50}$ confirmed through the reading result were shown in FIG. 2. In addition, enzyme activity assay was performed under the same conditions except for the treatment of each concentration of MKI-1 (0, 6.25, 12.5, 25, 50 and 100 μM) through western blot, and it was shown in FIG. 3.

Figure 2:
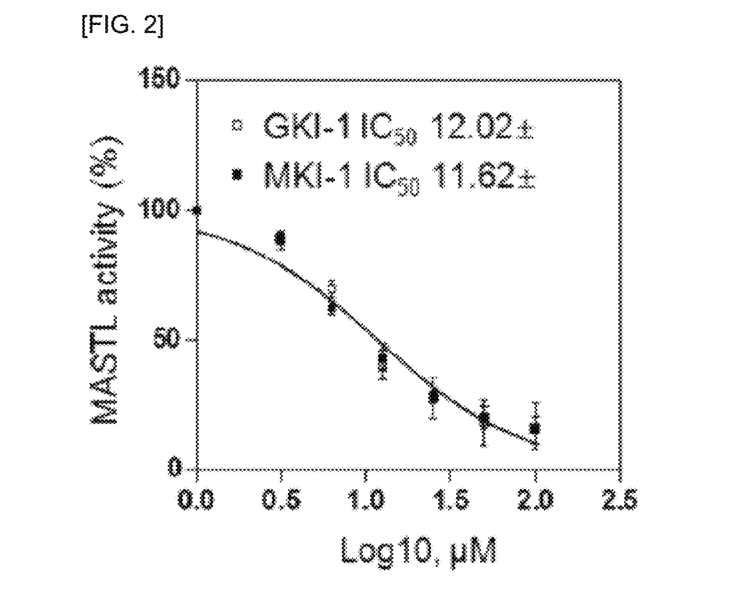
FIG. 2 shows the results of ADP-Glo kinase activity and $IC_{50}$ value from the treatment of MKI-1 (N-1H-benzimidazol-2-yl-3-(1H-pyrrol-1-yl) benzamide) and GKI-1 at various concentrations (0-100 μM).

As shown in FIG. 2, as a result of calculating the $IC_{50}$ value, it was confirmed that it was 11.62 μM when MKI-1 was treated, which is similar to the value of GKI-1 used as a positive control representing a value of 12.02 μM.

Figure 3:
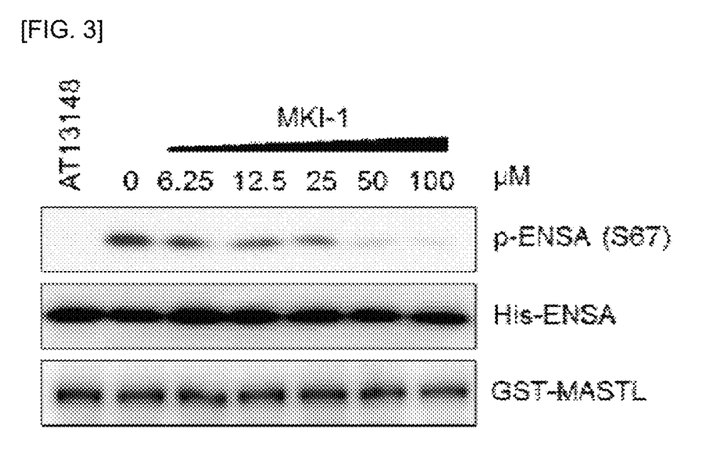
FIG. 3 shows the results of analyzing the inhibition of MASTL kinase activity the treatment of MKI-1 and GKI-1 at various concentrations (0-100 μM) in vitro.

In addition, as shown in FIG. 3, the higher the treatment dose of MKI-1, the more efficient inhibition of ENSA phosphorylation and thus the dose-dependent MASTL kinase inhibitory effect was confirmed. In particular, it was confirmed that when MKI-1 was treated with 50 μM or more, p-ENSA did not appear, which could completely inhibit the activity of MASTL kinase. Accordingly, it was confirmed that the MKI-1 treatment can effectively inhibit the activity of MASTL kinase, and the inhibition as described above is dose dependent.

Example 4. Confirmation of MASTL Kinase Inhibitory Effect of Selected N-1H-benzimidazol-2-yl-3-(1H-pyrrol-1-yl) benzamide (MKI-1) in Cancer Cell Lines An experiment was conducted to confirm whether the selected MKI-1 can inhibit the activity of MASTL kinase and thus also effectively inhibit ENSA phosphorylation in breast cancer cell lines. Treatment with MASTL kinase inhibitors (MKI-1 and GKI-1) and immunofluorescence staining was performed using an antibody against phosphorylated ENSA (Ser67)/ARPP19 (ser62) to confirm by fluorescence whether the expression of phosphorylated ENSA is effectively inhibited in the breast cancer cell line MCF7. After culturing $2.5 \times 10^4$ MCF7 cells in a 6-well plate for 24 hours, 80 ng/mL of a MASTL kinase inhibitor and a cell cycle control agent Colcemid (KaryoMAX™ Colcemid™ Solution in PBS; Gibco) were treated for 16 to 18 hours. After washing with phosphate buffered saline for fixation and permeabilization of cells, 4% paraformaldehyde and 0.2% Triton-X were added and reacted for 10 minutes, respectively. After 1 hour pretreatment with 5% fetal bovine serum, 1:100 diluted antibody against phosphorylated ENSA (Ser67)/ARPP19 (ser62) was treated for 16 hours, and then it was washed with 0.1% Triton X-100/phosphate buffered saline solution (Tritonx-100/PBS) 3 times. Alexa488-conjugated secondary antibody (AP132JA4, Invitrogen) was reacted for 2 hours at room temperature to label, and phosphorylated ENSA was photographed and analyzed using IN Cell Analyzer 6000 (GE Healthcare Life Science). The results of the experiment are shown in FIG. 4A and the degree of phosphorylation was schematically shown in FIG. 4B.

Figure 4:
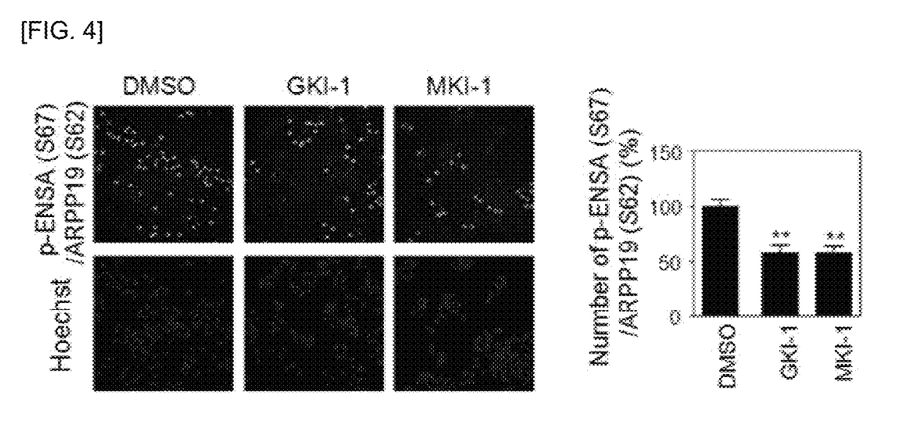
FIG. 4 shows the results of expression of phosphorylated ENSA when the breast cancer cell line MCF7 was treated with MKI-1 at various concentrations (0-100 μM).

As shown in FIG. 4A and FIG. 4B, it was confirmed that MKI-1 exhibited a phosphorylation inhibitory activity of ENSA at a level close to about half of that of DMSO used as a control. In particular, it was confirmed that it exhibits a similar degree of phosphorylation inhibitory effect to GKI-1 used as a positive control, and that M phase of cancer cells can be inhibited through effective inhibition of ENSA phosphorylation in breast cancer cell lines.

Example 5. Confirmation of MASTL Kinase-Specific Inhibitory Effect of Selected N-1H-benzimidazol-2-yl-3-(1H-pyrrol-1-yl) benzamide (MKI-1)

Western blotting assay was performed to confirm whether the selected MKI-1 exhibits MASTL kinase-specific inhibitory activity. 20 μg of protein was separated by SDS-PAGE electrophoresis and transferred to a PVDF membrane, and the following specific antibodies were used: rabbit polyclonal antibody MASTL (Abgent); phospho-ENSA (Ser67)/ARPP19 (Ser62) (#5240), ENSA (#11915S), cleaved PARP (Asp214) (#9541), AKT (#9272), phospho-AKT (ser473) (#9271), phospho-GSK-3α/β (Ser21/9) (#9331), phospho-p70S6K (The 288) (#9205) and phospho-Chk2 (Thr68) (#2661; Cell Signaling Technology, MA); p70S6K (sc-230; Santa Cruz Biotechnology, CA, USA), phospho-H3 (S10) (06-570, Merck, NJ); mouse monoclonal antibody caspase-2 (#2224S). In addition, mouse polyclonal antibody β-actin (C4; Santa Cruz Biotechnology, CA, USA) was used as a loading control, it was washed with 1×PBS/0.1% Tween 20, and the binding protein was detected using HRP-binding secondary antibody and improved chemiluminescence detection system. The remaining conditions of Western blotting were the same as in Example 3, and the image of the band was obtained by Amersham Imager 600 system (GE Healthcare Life Science) or X-Ray film (AG, HealthCare, SC, USA) and it was shown in FIG. 5.

Figure 5:
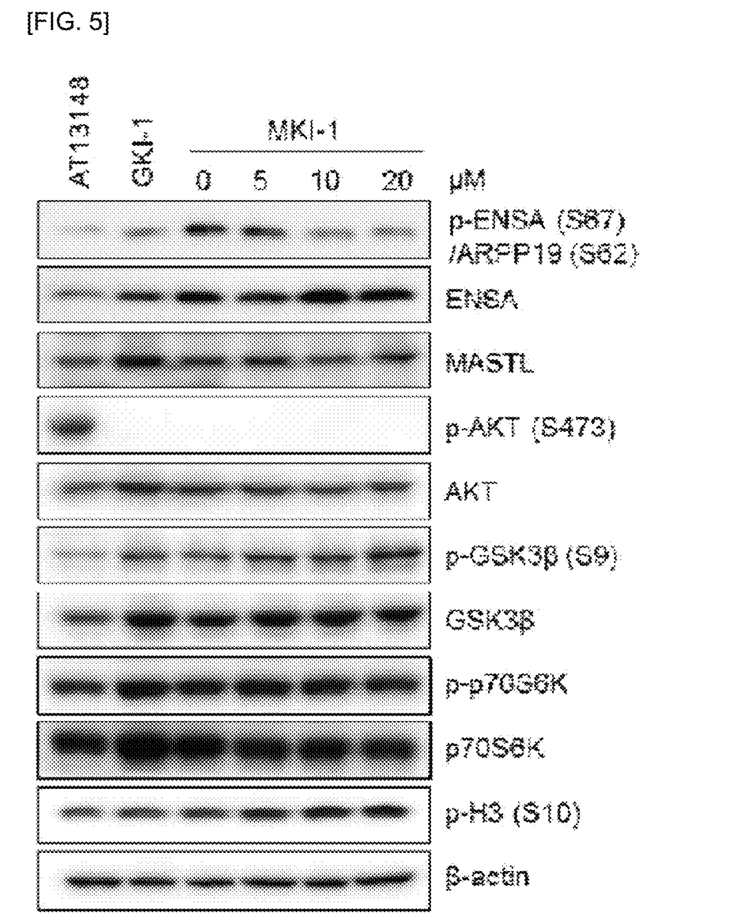
FIG. 5 shows the results of analyzing the inhibition of various kinase activities induced by treating a breast cancer cell line (MCF7) with a pan-kinase inhibitor (AT13148), MASTL kinase inhibitors MKI-1 and GKI-1.

As shown in FIG. 5, AT13148 used as a control strongly inhibited the activation of AKT in MCF7 cells, and changed the expression levels of AKT phosphorylated and GSK-3P phosphorylated by AT13148. On the other hand, it was confirmed that MKI-1 only reduced the expression level of phosphorylated p-ENSA in MCF7 cells in a dose-dependent manner, but did not regulate the activities of AKT and phosphorylated GSK-3P. In addition, MKI-1 increased the expression level of phosphorylated H3 in a dose-dependent manner and when the expression of phosphorylated H3 increases, mitosis stops and thus as a result, it was confirmed that MKI-1 can stop the mitosis of cancer cells. Overall, it was confirmed that MKI-1 can effectively inhibit only the kinase activity of the target MASTL without affecting the activity of other AGC kinases.

Example 6. Confirmation of Cancer Cells-Specific Killing Effect (Anticancer Effect) of Selected N-1H-benzimidazol-2-yl-3-(1H-pyrrol-1-yl) benzamide (MKI-1)

6.1 Confirmation of Cancer Cell-Specific Killing Effect of MKI-1

In order to confirm whether the selected MKI-1 can kill only cancer cells, an experiment was performed by treating with MKI-1 and measuring whether the cell viability of breast cancer cell lines and normal cell lines was changed. WST-8 analysis (Cyto X™ cell viability assay kit, LPS solution, Daejeon, Korea) was performed according to the manufacturer's protocol. Cancer cells MCF7 and BT549 and normal cell line MCF10A cells were inoculated into a 96-well plate, cultured for 24 hours, and then treated with MASTL kinase inhibitors at various concentrations (3.70, 11.11, 33.33 and 100 µM). Thereafter, the absorbance was measured at 450 nm using a Versamax micro plate reader (Molecular Devices, CA, USA), and the results were shown in FIG. 6.

Figure 6:
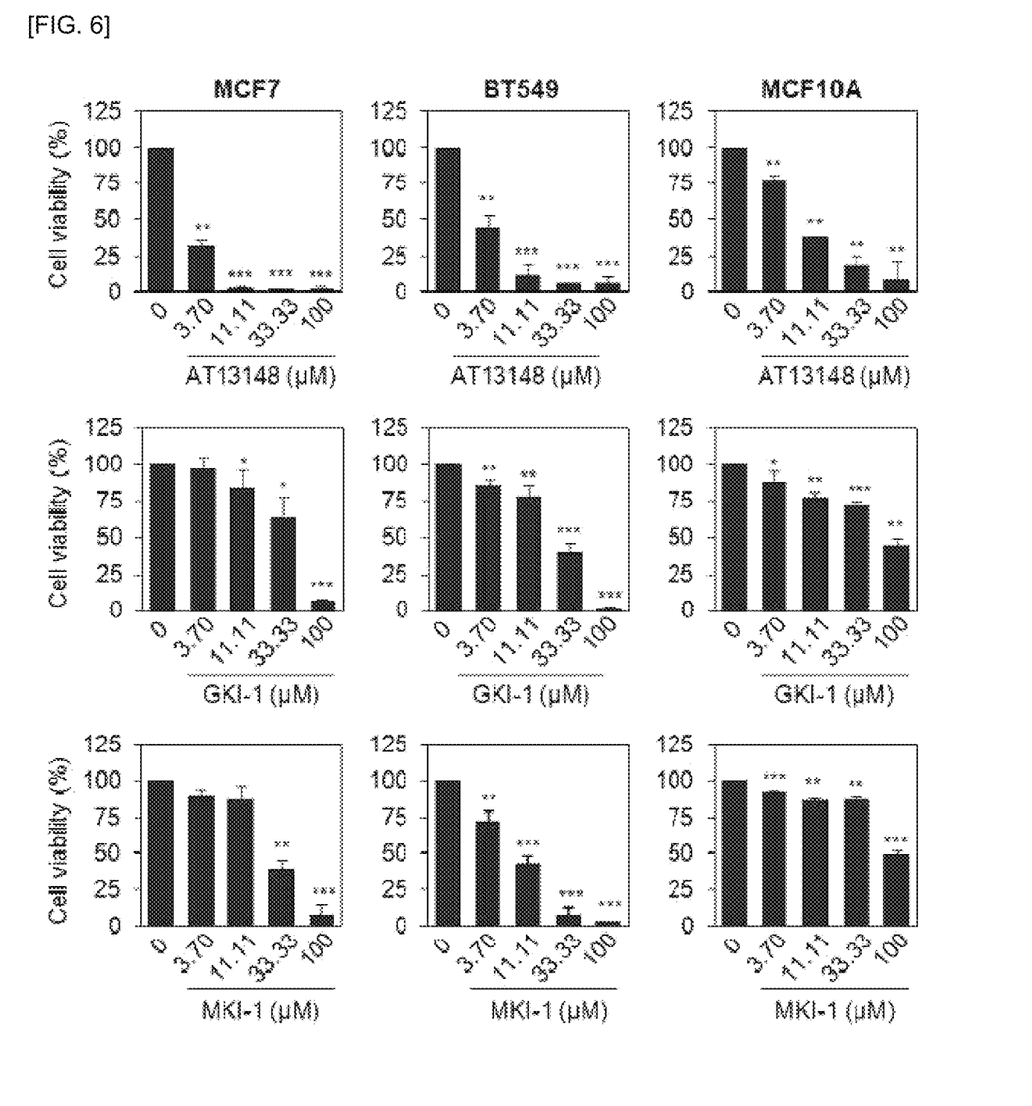
FIG. 6 shows the cell viability when breast cancer cell lines MCF7 and BT549, and the normal cell line (MCF10A) were treated with MKI-1.

As shown in FIG. 6, it was confirmed that AT13148 used as a positive control group drastically reduced cell viability without distinguishing between cancer cells and normal cell lines. In particular, it was confirmed that MKI-1 and GKI-1 hardly decrease cell viability when treated with normal cell lines, but can exhibit anticancer activity that decreases cell viability in a dose-dependent manner in cancer cell lines (MCF7 and BT549). In particular, in cancer cell lines, MKI-1 of 33.33 µM or more significantly reduced the survival rate of cancer cells, and particularly, when treated with the same dose, the cell viability significantly decreased in the group treated with MKI-1 than in GKI-1. Therefore, even when the dose and specificity were compared, it was confirmed that MKI-1 has remarkably superior cancer cell-specific killing effects than other kinase inhibitors.

Example 6.2 Confirmation of Cancer Cell Killing Effect (Anti-Cancer Effect) Through Colonogenic Assay of MKI-1

Colony formation analysis was performed to confirm whether the selected MKI-1 can effectively kill cancer cells. First, breast cancer cells MCF7 (500-1000 cells) were cultured in a 60 mm culture plate, and after 24 hours, it was treated with MASTL kinase inhibitors (AT13148, MKI-1 and GKI-1), respectively and cultured for 15 days. Cells were fixed and stained with tryptophan blue to which methanol was added to quantify the number of colonies, which was shown in FIG. 7.

Figure 7:
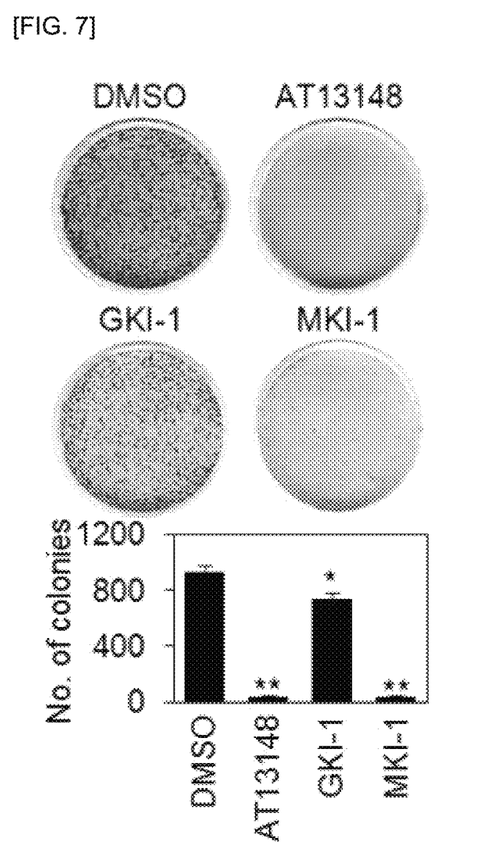
FIG. 7 shows the results of analyzing a cancer cell line colony formation when a breast cancer cell line (MCF7) was treated with pan-kinase inhibitors (AT13148), MASTL kinase inhibitors MKI-1 and GKI-1.

As shown in FIG. 7, it was confirmed that in the group treated with GKI-1 compared to DMSO as a control group, the number of cell colonies of cancer cell lines hardly decreased, and GKI-1 hardly reduced the colonies of cancer cells. On the other hand, in the MKI-1 treatment group, it was confirmed that cancer cell colonies were significantly reduced to a similar degree to that of the group treated with AT13148 used as a positive control group. Therefore, it was confirmed that MKI-1 can effectively kill the colonies of cancer cells.

Example 6.3 Confirmation of Cancer Cell Killing Effect (Anti-Cancer Effect) Through Tumorsphere Forming Assay of MKI-1

A tumorsphere formation assay was performed in order to determine whether the selected MKI-1 can effectively reduce the formation of tumorsphere in cancer cells, Breast cancer cells MCF7 (2500-10000 cells) was suspended in serum-free DMEM/F12 (weIGENE) containing 1% penicillin, B-27 (1:50; invitrogen), 20 ng/mL epidermal cell growth factor (R&D Systems) and 20 ng/mL fibroblast growth factor (R&D Systems) and cultured on plates with low adhesion rate. After 24 hours, the cells were treated with MASTL kinase inhibitors (AT13148, MKI-1 and GKI-1), respectively, and cultured for 15 days, and then the diameter of the tumorsphere was measured and quantified, which was shown in FIG. 8.

Figure 8:
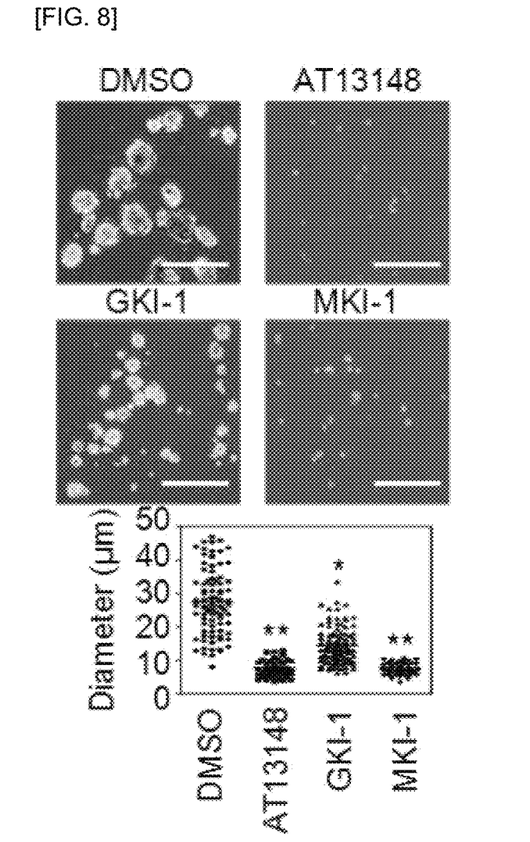
FIG. 8 shows the results of analyzing sphere formation of a cancer cell line when a breast cancer cell line (MCF7) was treated with a pan-kinase inhibitor (AT13148), MASTL kinase inhibitors MKI-1 and GKI-1.

As shown in FIG. 8, it was confirmed that in the group treated with GKI-1, the diameter of the cell tumor cells of the cancer cell line was hardly decreased compared to DMSO as a control group, and that GKI-1 did not decrease the size of the cancer cells. On the other hand, it was confirmed that in the MKI-1 treatment group, the tumorsphere diameter of the cancer cell significantly decreased to a similar degree to that of the AT13148 treatment group used as a positive control group. Therefore, it was confirmed that MKI-1 can effectively reduce the size of tumorsphere in cancer cells and also effectively reduce the formation of tumorsphere.

Example 6.4 Confirmation of Cancer Cell Killing Effect (Anti-Cancer Effect) Through 3-D Culture of MKI-1 (Three-Dimensional Culture)

Figure 9:
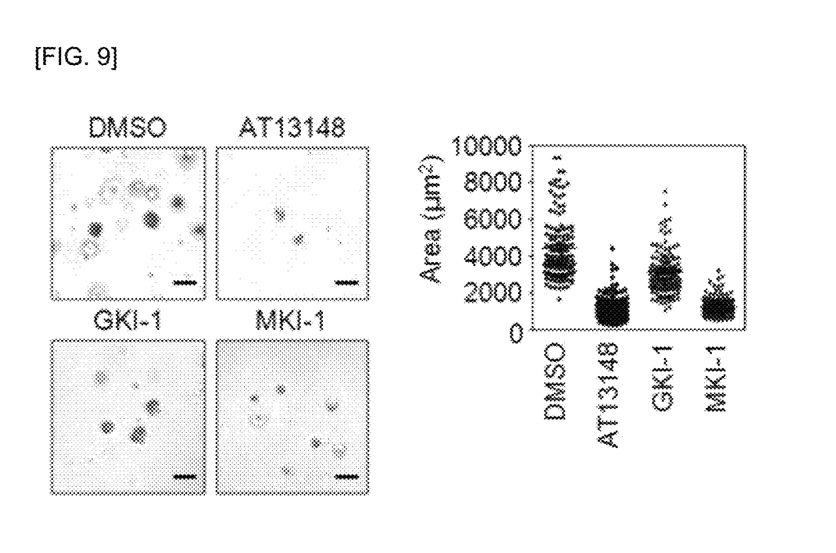
FIG. 9 shows the results of analyzing spheroid formation in a 3D culture environment when a breast cancer cell line (MCF7) was treated with pan-kinase inhibitor (AT13148), MASTL kinase inhibitors MKI-1 and GKI-1.

In order to confirm whether the selected MKI-1 can effectively inhibit the proliferation of cancer cells even in 3-D culture similar to the environment of the extracellular matrix (ECM), an experiment was performed to confirm the cancer cell killing effect. 3D culture was performed according to the protocol of the manufacturing company TheWell Bioscience. It was inoculated into 24-wells containing a DMEM mixture containing 10,000 MCF7 cells in an MCF7 cell:hydrogel solution in a ratio of 1:3 (v/v) and VitroGel™ 3D-RGD diluted with 0.1% PBS in a ratio of 1:3 (v/v) of a hydrogel:diH2O. Thereafter, incubation was performed at 37° C. for 15 minutes to stabilize the VitroGel 3D-RGD hydrogel. To cover the hydrogel, the same volume of DMEM as the hydrogel was added, and the next day, the hydrogel was treated with a DMSO base drug containing DMSO, AT13148 (2 µM), GKI-1 (10 µM) and MKI-1 (10

μM). The medium was exchanged every 2 days for 14 to 20 days. Thereafter, the area of the spheroid was measured with a DIXI image solution, and the results were shown in FIG. 9.

As shown in FIG. 9, it was confirmed that in the group treated with GKI-1, which is a control, the size of the spheroid of the cancer cell line was hardly decreased compared to DMSO, and that GKI-1 hardly decreased the cancer cell spheroid. On the other hand, in the MKI-1 treatment group, the size of the cancer cell spheroids was significantly reduced to a similar degree to that of the group treated with AT13148 used as a positive control. Therefore, it was confirmed that MKI-1 can effectively inhibit the formation of cancer cell spheroids even in a 3-D culture environment similar to that in a natural extracellular matrix.

Accordingly, it was confirmed that MKI-1 shows a killing effect only on cancer cells without affecting the cell viability of normal cells, and can effectively inhibit the formation of colonies, tumorsphere formation and spheroid formation in cancer cells and thus it can be effectively used as an active ingredient of an anticancer drug.

Example 7. Confirmation of Synergistic Effect of Radiation Sensitivity of Cancer Cell Lines Through Treatment of Selected N-1H-benzimidazol-2-yl-3-(1H-pyrrol-1-yl) benzamide (MKI-1)

Figure 10:
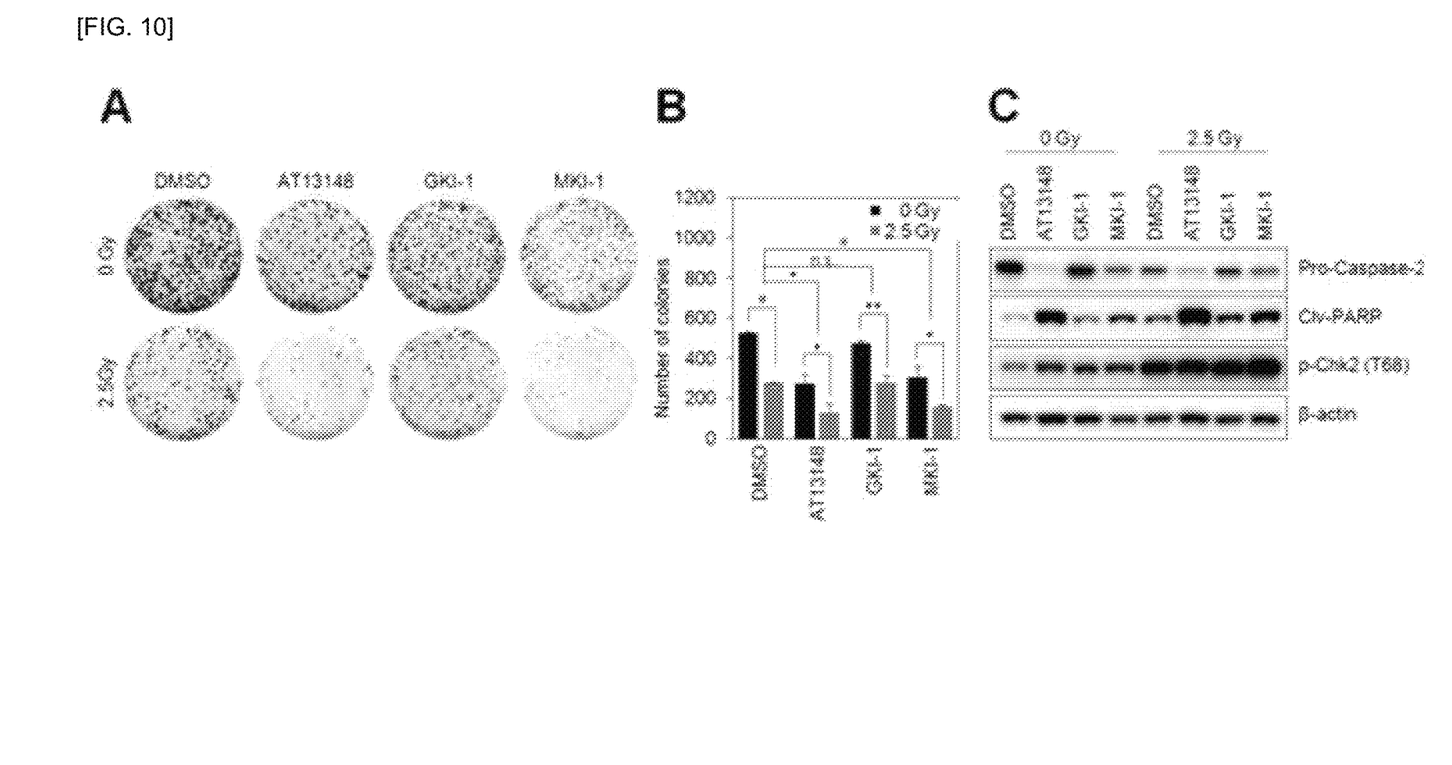
FIG. 10 shows the result of cancer cell colony formation (FIG. 10A), and the result of numerically displaying the colony formation (FIG. 10B) and the result of performing Western blot (FIG. 10C) when a breast cancer cell line (MCF7) was treated with radiation and pan-kinase inhibitor (AT13148), MASTL kinase inhibitors MKI-1 and GKI-1.

7.1 Confirmation of Synergistic Effect of Radiation Sensitivity of MCF7 Cancer Cell Lines Through MKI-1 Treatment A colonogenic assay was performed in order to confirm whether the sensitivity to the radiation treatment effect can be increased when MCF7 cancer cell line was treated with MKI-1. First, breast cancer cells MCF7 (500-1000 cells) were placed in a 60-mm tissue culture medium on a 60 mm culture plate, and treated with MASTL kinase inhibitors (AT13148, MKI-1 and GKI-1), respectively, and then was treated with 2.5 Gy radiation by Biobeam GM8000 (Gamma-Gamma-Service Medical GmbH, Leipzig, Germany) and the control group was not treated with radiation. After 10 to 14 days, the cell colonies were fixed with methanol and stained with 0.5% crystal violet, and the results were shown in FIG. 10A, and the number of colonies shown in the above results was quantified using Image J software to show in 10B, and then western blotting was performed and the results thereof were shown in FIG. 10C.

As shown in FIG. 10A and FIG. 10B, in the group treated with GKI-1, there was no synergistic effect on the sensitivity of cancer cells to radiation therapy due to the compound treatment, similarly to the group treated with DMSO. On the other hand, it was confirmed that in the group treated with MKI-1, the radiotherapy effect of the MCF-7 cancer cell line was significantly higher than that of the group treated with DMSO, and the number of cancer cell colonies decreased. In particular, as shown in FIG. 10C, it was confirmed that the expression levels of cleaved-PARP and phosphorylated Chk2 increased, and the expression levels of procaspase-2 decreased in the group treated with MKI-1 after radiation treatment. Through the above results, it was confirmed that the cancer cells can be effectively killed. Therefore, in summary, it was confirmed that MKI-1 can be effectively used as a radiosensitizer in cancer cells.

Figure 11:
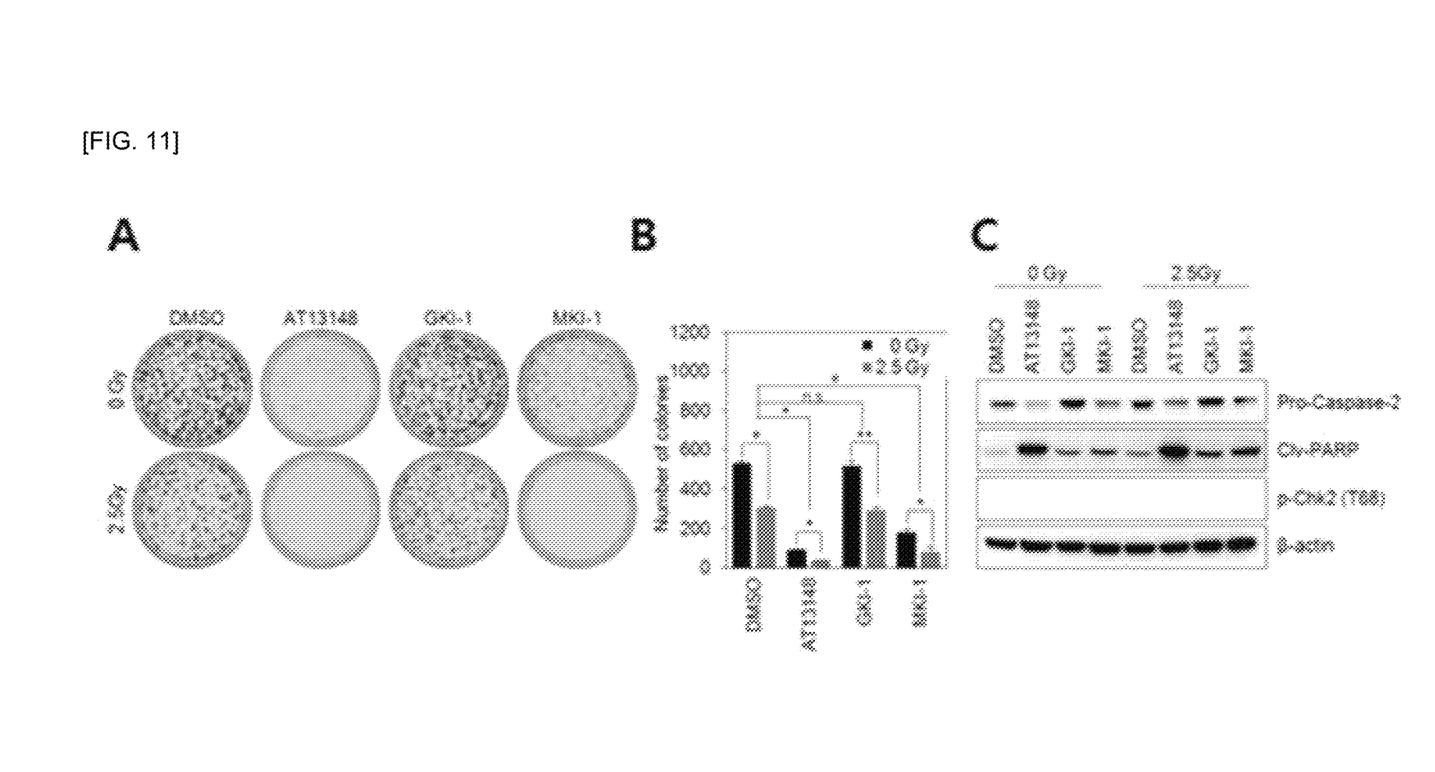
FIG. 11 shows the results of cancer cell colony formation (FIG. 11A), and the result of numerically displaying the colony formation (FIG. 11B) and the result of performing Western blot (FIG. 11C) when a breast cancer cell line having a radioresistant phenotype ($CD44^{high}/CD24^{low}$ MCF7) was treated with radiation and pan-kinase inhibitor (AT13148), MASTL kinase inhibitors MKI-1 and GKI-1.

7.2 Confirmation of Synergistic Effect of Radiation Sensitivity of MCF7 Cancer Cell Lines with Radioresistant Phenotype Through MKI-1 Treatment A colonogenic assay was performed in order to confirm whether the sensitivity to the radiation treatment effect was increased even in the CD44$^{high}$/CD24$^{low}$ MCF7 cancer cell line having a radioresistant phenotype, when it was treated with MKI-1. First, breast cancer cells CD44$^{high}$/CD24$^{low}$ MCF7 (500-1000 cells) were placed in a 60-mm tissue culture medium on a 60 mm culture plate, and treated with MASTL kinase inhibitors (AT13148, MKI-1 and GKI-1), respectively, and then was treated with 2.5 Gy radiation by Biobeam GM8000 (Gamma-Gamma-Service Medical GmbH, Leipzig, Germany) and the control group was not treated with radiation. After 10 to 14 days, the cell colonies were fixed with methanol and stained with 0.5% crystal violet, and the results were shown in FIG. 11A, and the number of colonies shown in the above results was quantified using Image J software to show in 11B, and then western blotting was performed and the results thereof were shown in FIG. 11C.

As shown in FIG. 11A and FIG. 11B, in the group treated with GKI-1, there was no synergistic effect on the sensitivity of cancer cells to radiation therapy due to the compound treatment, similarly to the group treated with DMSO. On the other hand, in the MKI-1-treated group, the MCF-7 cancer cell line showed a significant increase in sensitivity to radiation treatment compared to the DMSO-treated group, indicating that the number of cancer cell colonies was remarkably reduced. In particular, the above result indicated a more significant reduction than the synergistic effect of the sensitivity in Example 7.1, and it was confirmed that the cancer cell line, a radioresistant phenotype, exhibited a remarkable synergistic effect of the sensitivity due to treatment with MKI-1. In addition, as shown in FIG. 11C, it was confirmed that the expression levels of cleaved-PARP and phosphorylated Chk2 increased, and the expression levels of procaspase-2 decreased in the group treated with MKI-1 after radiation treatment. Through the above results, it was confirmed that the cancer cells can be effectively killed.

Accordingly, it was confirmed that MKI-1 is a material that can be used more effectively as a radiosensitizer since it can more effectively increase the sensitivity to radiation in cancer cells exhibiting radioresistance.

The invention claimed is:

1. A method of treating cancer in a subject in need thereof, comprising:
    administering a pharmaceutical composition comprising N-1H-benzimidazol-2-yl-3-(1H-pyrrol-1-yl) benzamide represented by following Chemical Formula, a derivative thereof, or a pharmaceutically acceptable salt thereof as an active ingredient to the subject,
    wherein the cancer is at least one selected from the group consisting of brain tumor, benign astrocytoma, malignant astrocytoma, pituitary adenoma, meningioma, cerebral lymphoma, oligodendroglioma, intracranial tumor, ependymoma, brain stem tumor, head and neck tumor, laryngeal cancer, oropharyngeal cancer, nasal and paranasal cavity cancer, nasopharyngeal cancer, salivary gland cancer, hypopharyngeal cancer, thyroid cancer, thoracic tumor, small cell lung cancer, non-small cell lung cancer, thymus cancer, mediastinal tumor, esophageal cancer, breast cancer, male breast cancer, abdominal tumor, gastric cancer, liver cancer, gallbladder cancer, biliary tract cancer, pancreatic cancer, small intestine cancer, colon cancer, anal cancer, bladder cancer, kidney cancer, male genital tumor, penile cancer, urethral cancer, prostate cancer, female genital tumor, cervical cancer, endometrial cancer, ovarian cancer, uterine sarcoma, vaginal cancer, vulva cancer, female urethral cancer, skin cancer, myeloma, leukemia and malignant lymphoma:

[Chemical Formula]

2. The method of claim 1, wherein the pharmaceutical composition inhibits an activity of microtubule-associated serine/threonine kinase-like (MASTL) kinase.

3. The method of claim 1, wherein the pharmaceutical composition reduces an expression level of phosphorylated endosulfine alpha.

4. The method of claim 1, wherein the pharmaceutical composition arrests mitosis of cancer cells or induces apoptosis of cancer cells.

5. The method of claim 1, wherein the pharmaceutical composition is used in combination with radiation therapy.

6. The method of claim 1, wherein the pharmaceutical composition increases sensitivity to radiation of cancer cells or cancer cells with radioresistance.

7. The method of claim 1, wherein the pharmaceutical composition restores or enhances radiation sensitivity by inhibiting an activity of MASTL kinase.

\* \* \* \* \*